United States Patent [19]

Brainard, II

[11] 4,297,685

[45] Oct. 27, 1981

[54] APPARATUS AND METHOD FOR SLEEP DETECTION

[75] Inventor: Edward C. Brainard, II, Marion, Mass.

[73] Assignee: Environmental Devices Corporation, Marion, Mass.

[21] Appl. No.: 44,268

[22] Filed: May 31, 1979

[51] Int. Cl.³ .............................................. G08B 21/00
[52] U.S. Cl. .................................... 340/575; 128/736; 340/573
[58] Field of Search ................. 340/575, 573; 128/736

[56] References Cited

U.S. PATENT DOCUMENTS

| | | | |
|---|---|---|---|
| 3,054,397 | 9/1962 | Benzinger | 128/736 |
| 3,082,414 | 3/1963 | Papaminas | 340/575 |
| 3,274,994 | 9/1966 | Sturm | 128/736 |
| 3,282,106 | 11/1966 | Barness | 73/355 |
| 3,491,596 | 1/1970 | Dean | 128/736 |

OTHER PUBLICATIONS

Heller, et al., "The Thermostat of Vertebrate Animals", *Scientific American,* 239:16–17, 102–110+, Aug. 1978.

*Primary Examiner*—Glen R. Swann, III

[57] ABSTRACT

The invention rests on the discovery that the onset of sleep is preceeded by a drop in brain temperature as measured within the auditory canal. Auditory canal temperature is thus measured and its value used to activate an audible or visible alarm to prevent the subject's falling asleep.

13 Claims, 7 Drawing Figures

APPARATUS AND METHOD FOR SLEEP DETECTION

BACKGROUND OF THE INVENTION

This invention relates to the detection of the onset of sleep in a human being and more particularly to such detection by monitoring temperature variations within the auditory canal.

There has been a long-standing need for reliable techniques to detect the onset of sleep. Such techniques would be particularly advantageous for preventing accidents by those who drive trucks or cars for long periods of time or operate other potentially dangerous machinery. Prior approaches for detecting the oncoming condition of sleep and thereafter stimulating the subject to prevent an accident have not been altogether satisfactory. Techniques which monitor such parameters as a subject's eye movements, breathing rate, electroencephalogram, or electrocardiogram are cumbersome and are often incapable of detecting reliably the onset of sleep. Similarly, a so-called dead man's grip which senses relaxation of the subject's grip to indicate a sleep state, although not difficult to implement, may not respond soon enough to prevent an accident.

In occupations requiring mental alertness such as air traffic control, it is likewise desirable to detect a diminution in mental acuity short of the subject's actually falling asleep so that he may be replaced by someone more mentally alert. Heretofore, there has been no simple and reliable way of detecting the often subtle degradation in alertness.

It is therefore an object of the present invention to provide apparatus for detecting the onset of sleep which is reliable, easy to implement and which interferes minimally with the subject's comfort and mobility.

It is a further object to provide apparatus capable of detecting a falloff in mental alertness in a human subject.

SUMMARY OF THE INVENTION

This invention is based on the discovery that the temperature of the human brain as measured within the auditory canal varies with changes in levels of alertness. Specifically, it has been found that as mental activity or alertness decreases, the temperature of the brain decreases; upon the onset of sleep, the temperature will drop by approximately 0.5° to 1.5° F. Conversely, brain temperature increases with increased mental activity. That temperature within the auditory canal decreases as a subject falls asleep thus affords a way of detecting the onset of sleep.

The apparatus for detecting the onset of sleep in a human being according to the present invention employs means including a temperature responsive sensor, for measuring the temperature within the auditory canal. Comparator means then produces an output signal when the temperature drops below a predetermined value. In another embodiment of the invention, the temperature measuring means is interconnected with a differentiator means for generating the time rate of change of the temperature. A comparator means produces an output signal when the time rate of change of temperature exceeds a predetermined value.

Another implementation of the invention involves means for generating a running average of the time series of measured temperatures within the auditory canal. The present temperature is then compared with the running average and a comparator produces an output signal when the temperature falls below the running average by a predetermined value.

In yet another important embodiment of the invention for detecting the onset of sleep in a particular individual, the temperature as measured within the auditory canal is compared with the previously determined normal circadian temperature variations for that individual over a time period. These circadian variations are preserved by conventional signal storing means. An output signal is produced when the measured temperature at a given time drops below the corresponding circadian temperature by a predetermined value.

In a still further embodiment, the temperature as measured within the auditory canal is compared with the body core temperature of the individual, and an output signal is generated when the auditory canal temperature falls below the body core temperature by a predetermined amount.

And in yet another embodiment a subject is monitored to determine the auditory canal temperature at the onset of sleep. This temperature is then used as the reference temperature at which an alarm will be activated.

The above described embodiments may also be used to detect a diminution in mental acuity short of the subject's actually falling asleep by comparing the temperature within the auditory canal with a predetermined value. Similarly, a state of heightened mental activity can be detected by observing an increase in auditory canal temperature above a predetermined value.

In the embodiments of the invention described above, auditory canal temperature may be measured in several ways. A preferred method comprises a temperature responsive sensor in a heat conduction relationship with the auditory meatus or with the tympanic membrane itself. Another preferred method comprises an infrared sensor disposed within the auditory canal for receiving infrared radiation. In the above embodiments, the output signal is adapted to activate an audible or visible alarm.

BRIEF DESCRIPTION OF THE DRAWING

The invention disclosed herein will be better understood in relation to the following drawing of which.

DESCRIPTION OF THE PREFERRED EMBODIMENT

Figure 1:
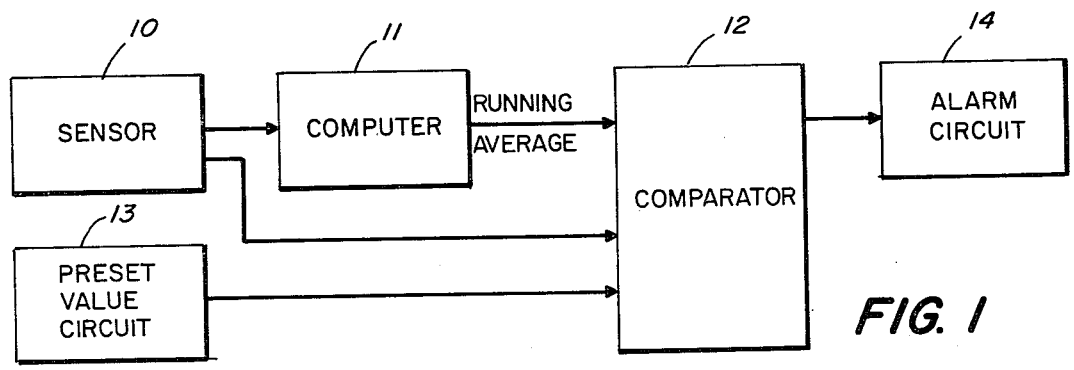
FIG. 1 is a schematic diagram of the invention using a running average of the auditory canal temperature.

Referring first to FIG. 1, sensor 10 is a temperature responsive sensor such as a thermistor as disclosed in U.S. Pat. No. 3,054,397 or an infrared detector as described in U.S. Pat. No. 3,282,106. If a thermistor or thermocouple junction is used as the temperature sensing device, it is placed in physical contact with the tympanic membrane or the external auditory meatus.

The output of sensor 10 is connected both to a computer 11 and to a comparator 12. The computer 11, of conventional design, computes the running average of the time series of auditory canal temperatures. This running average forms the second input into the comparator 12. The third input to the comparator 12 comes from the preset value circuit 13 which simply enters a scalar number into the comparator 12. The comparator 12 generates an output signal when the current temperature value falls below the running average by the preset value supplied by circuit 13. A preferred preset value range is 0.5° to 1.5° F. The output signal from the comparator 12 activates the alarm circuit 14 which may be an audible or visible alarm or both.

Figure 2:
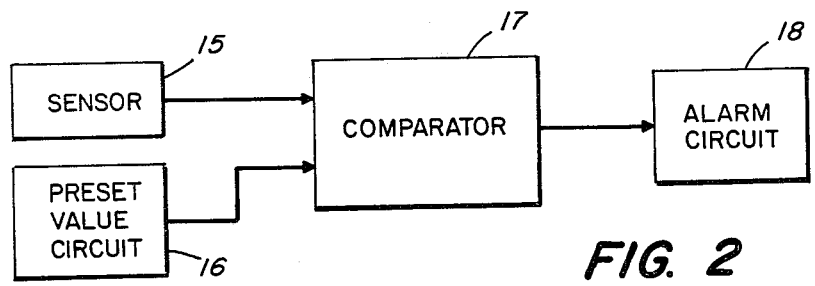
FIG. 2 is a schematic diagram of an embodiment using a preset activation temperature.

FIG. 2 shows an implementation of the invention in which the temperature within the auditory canal as measured by sensor 15 is compared with a preset value from the circuit 16 by a comparator 17. The comparator 17 produces an output signal which activates an alarm circuit 18 when the present temperature drops below a preset value, e.g., 0.5° to 1.5° F. below normal body temperature.

Figure 3:
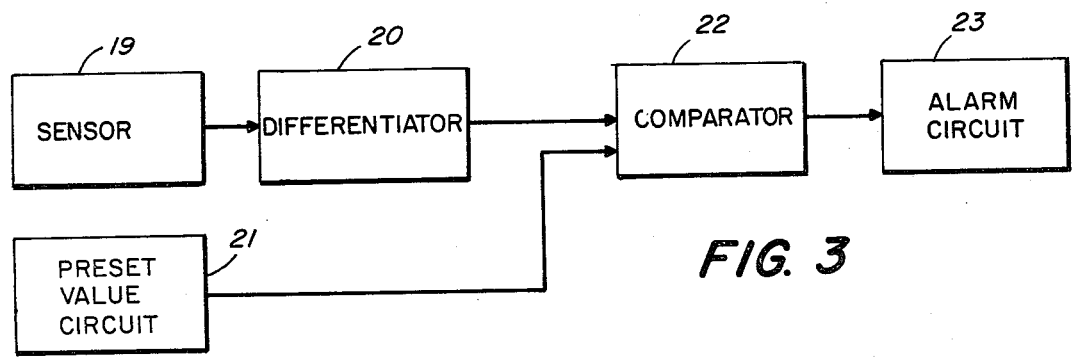
FIG. 3 is a schematic diagram showing the use of the time rate of change of temperature.
Figure 4:
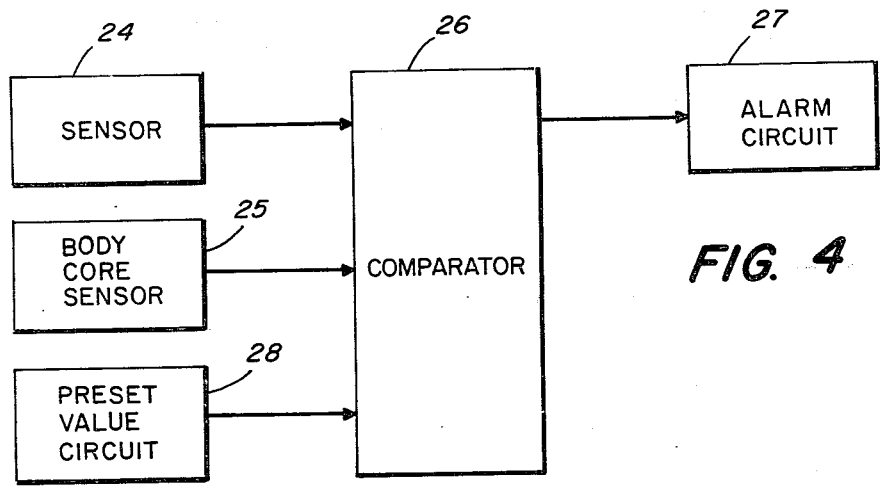
FIG. 4 is a schematic diagram showing the use of body core temperature.

An important embodiment of the invention is shown in FIG. 3. The output of the temperature sensor 19 is differentiated with respect to time by the differentiator 20 which is a conventional analog or digital circuit. This time rate of change of temperature is compared with a preset value from the circuit 21 by comparator 22 which activates the alarm circuit 23 when the output of differentiator 20 exceeds the preset value. In FIG. 4, two temperatures are measured. The sensor 24 measures temperature within the auditory canal as by an infrared detector or a thermistor. The temperature of the subject's body core is measured by a body core sensor 25. This sensor 25 may take the form of a thermistor detector which is placed, for example, in contact with the subject's armpit. A comparator circuit 26 produces an output signal to activate the alarm circuit 27 when the auditory canal temperature falls below the body core temperature by an amount as set by the preset value circuit 28. A preferred preset value range is 0.5° to 1.5° F.

Figure 5:
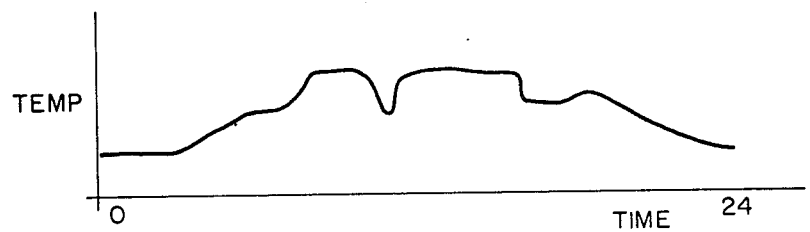
FIG. 5 is a graph of circadian temperature versus time.
Figure 6:
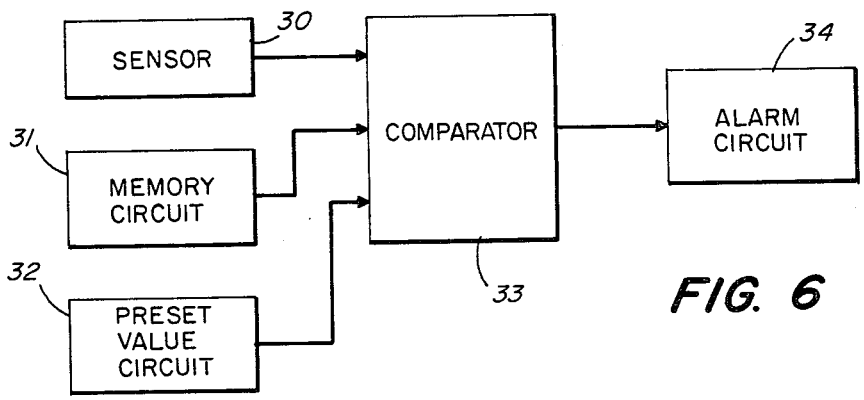
FIG. 6 is a schematic representation showing the use of the normal circadian temperature variations.

Referring now to FIG. 5, shown is a graph representing typical circadian temperature variations in a human being over a twenty four hour time period. Such a circadian temperature variation is used for sleep detection in the embodiment of this invention as depicted in FIG. 6. In this embodiment a particular subject is monitored for a 24 hour period and his circadian temperature profile is recorded by conventional techniques. For sleep detection, the present value of auditory canal temperature as measured by sensor 30 is compared with the previously stored circadian temperature value from the memory circuit 31. When the present temperature falls below the recorded circadian temperature by an amount as set in preset value circuit 32, the comparator 33 activates the alarm circuit 34. The use of previously determined circadian temperature variations allows for more reliable sleep onset detection as the normal temperature changes associated with eating or physical activity are thereby accounted for.

Figure 7:
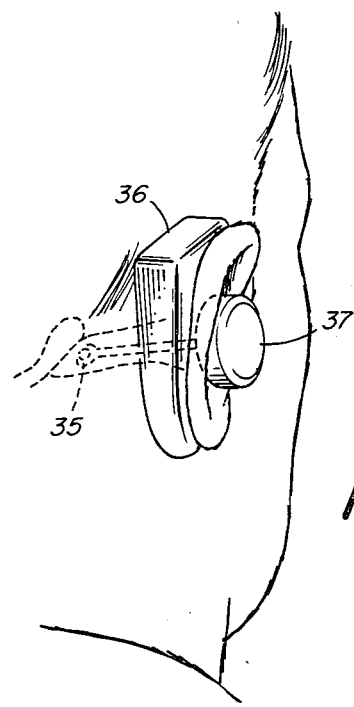
FIG. 7 is a diagrammatic representation of one embodiment of the invention.

FIG. 7 shows a preferred arrangement of the elements for the detection of the onset of sleep. A temperature sensor 35, e.g., a thermistor in contact with the tympanic membrane is connected to the electronics package 36 which rests upon the subject's outer ear. The electronics package 36 contains a comparator circuit which compares temperature as measured by sensor 35 with a preset value, for example, and activates an audible alarm 37 when the measured temperature falls below the preset value. It is to be understood that any of the embodiments of the invention described above may be implemented by the electronics package 36.

It is thus seen that the objects of this invention have been achieved in that simple and reliable techniques for detecting the onset of sleep have been described and disclosed. While the invention has been described with reference to its preferred embodiments, it is understood that modifications and variations will occur to those skilled in the art. Such modifications and variations are intended to fall within the scope of the appended claims.

What is claimed is:

1. Apparatus for detecting the onset of sleep in a human being, said apparatus comprising:
    means, including a temperature responsive sensor, for measuring the temperature within the auditory canal of said human being;
    differentiator means interconnected with said temperature measuring means for generating the time rate of change of said temperature; and
    comparator means for producing an output signal when said time rate of change of said temperature exceeds a predetermined value.

2. Apparatus for detecting the onset of sleep in a human being, said apparatus comprising:
    means, including a temperature responsive sensor, for measuring the temperature within the auditory canal of said human being;
    means for generating a running average of the time series of said temperature measurements; and
    comparator means for producing an output signal when said temperature drops below said running average by a predetermined value.

3. Apparatus for detecting the onset of sleep in a particular human being, said apparatus comprising:
    means, including a temperature responsive sensor, for measuring the temperature within the auditory canal of said particular human being;
    means for storing the previously determined normal circadian temperature variations within said auditory canal of said particular human being over a time period; and
    comparator means for producing an output signal when said temperature drops below said normal circadian temperature by a predetermined value.

4. Apparatus for detecting the onset of sleep in a human being, said apparatus comprising:
    means, including a temperature responsive sensor, for measuring the temperature within the auditory canal of said human being;
    means, including a second temperature responsive sensor, for measuring the body core temperature of said human being; and
    comparator means for producing an output signal when said temperature within said auditory canal drops below said body core temperature by a predetermined value.

5. The apparatus of claims 1, 2, 3, or 4, wherein said means for measuring said temperature within said auditory canal comprises a temperature responsive sensor in a heat conduction relationship with the auditory meatus.

6. The apparatus of claims 1, 2, 3, or 4, wherein said means for measuring said temperature within said auditory canal comprises an infrared sensor.

7. The apparatus of claims 1, 2, 3, or 4, wherein said means for measuring said temperature within said auditory canal comprises a temperature responsive sensor in a heat conduction relationship with the tympanic membrane.

8. The apparatus of claims 1, 2, 3, or 4, wherein said output signal is adapted to activate an audible alarm.

9. The apparatus of claims 1, 2, 3, or 4, wherein said output signal is adapted to activate a visual display.

10. Method for detecting the onset of sleep in a human being, said method comprising the steps of:
    (1) measuring the temperature within the auditory canal of said human being to produce a signal which varies with said temperature;
    (2) differentiating said signal to produce the time rate of change of said temperature;
    (3) comparing said time rate of change of said temperature with a predetermined value; and
    (4) generating an audible or visible alarm when said time rate of change of said temperature exceeds said predetermined value.

11. Method for detecting the onset of sleep in a human being, said method comprising the steps of:
    (1) measuring the temperature within the auditory canal of said human being;
    (2) computing a running average of the time series of said temperature measurements;
    (3) comparing said temperature with said running average; and
    (4) generating an audible or visible alarm when said temperature drops below said running average by a predetermined value.

12. Method for detecting the onset of sleep in a particular human being, said method comprising the steps of:
    (1) measuring the temperature within the auditory canal of said human being;
    (2) measuring and storing the previously determined normal circadian temperature variations within said auditory canal of said particular human being over a time period;
    (3) comparing said temperature with said normal circadian temperature at the time of measurement; and
    (4) generating an audible or visible alarm when said temperature drops below said circadian temperature by a predetermined value.

13. Method for detecting the onset of sleep in a human being comprising the steps of:
    (1) measuring the temperature within the auditory canal of said human being;
    (2) measuring the body core temperature of said human being;
    (3) comparing said auditory canal temperature with said body core temperature; and
    (4) generating an audible or visible alarm when said auditory canal temperature drops below said body core temperature by a predetermined value.

* * * * *